US010617761B2

(12) United States Patent
Albrecht

(10) Patent No.: US 10,617,761 B2
(45) Date of Patent: Apr. 14, 2020

(54) COMPOSITIONS AND SOLUTIONS FOR COLON CLEANSING

(71) Applicant: Regalismons S.A., Luxembourg (LU)

(72) Inventor: Uwe Willi Albrecht, Burgdorf (DE)

(73) Assignee: REGALISMONS S.A., Luxembourg (LU)

( * ) Notice: Subject to any disclaimer, the term of this patent is extended or adjusted under 35 U.S.C. 154(b) by 0 days.

(21) Appl. No.: 14/651,020

(22) PCT Filed: Dec. 12, 2013

(86) PCT No.: PCT/DE2013/000790
§ 371 (c)(1),
(2) Date: Jun. 10, 2015

(87) PCT Pub. No.: WO2014/090223
PCT Pub. Date: Jun. 19, 2014

(65) Prior Publication Data
US 2015/0320793 A1   Nov. 12, 2015

(30) Foreign Application Priority Data

Dec. 14, 2012   (DE) .................. 10 2012 024 434

(51) Int. Cl.
| | | |
|---|---|---|
| *A61K 45/06* | (2006.01) |
| *A61K 33/00* | (2006.01) |
| *A61K 31/77* | (2006.01) |
| *A61K 31/80* | (2006.01) |
| *A61K 33/06* | (2006.01) |
| *A61K 33/14* | (2006.01) |
| *A61K 9/48*  | (2006.01) |
| *A61K 33/10* | (2006.01) |
| *A61K 9/00*  | (2006.01) |
| *A61K 9/20*  | (2006.01) |
| *A61K 47/02* | (2006.01) |
| *A61K 9/08*  | (2006.01) |

(52) U.S. Cl.
CPC ............ *A61K 45/06* (2013.01); *A61K 9/0031* (2013.01); *A61K 9/08* (2013.01); *A61K 9/2009* (2013.01); *A61K 9/485* (2013.01); *A61K 31/77* (2013.01); *A61K 31/80* (2013.01); *A61K 33/00* (2013.01); *A61K 33/06* (2013.01); *A61K 33/10* (2013.01); *A61K 33/14* (2013.01); *A61K 47/02* (2013.01)

(58) Field of Classification Search
CPC ........ A61K 31/77; A61K 31/80; A61K 33/00; A61K 33/06; A61K 33/10; A61K 33/14; A61K 45/06; A61K 47/02; A61K 9/0031; A61K 9/08; A61K 9/2009; A61K 9/485
See application file for complete search history.

(56) References Cited

U.S. PATENT DOCUMENTS

| | | | | |
|---|---|---|---|---|
| 3,501,571 | A | * | 3/1970 | Yen ........................ A61K 9/145 |
| | | | | 424/456 |
| 7,169,381 | B2 | * | 1/2007 | Barras .................... A61K 9/009 |
| | | | | 424/78.01 |
| 2004/0253320 | A1 | | 12/2004 | Nijhawan |
| 2005/0244368 | A1 | | 11/2005 | Pashankar |
| 2008/0038336 | A1 | | 2/2008 | Esquea et al. |
| 2010/0297264 | A1 | * | 11/2010 | Kastenberg .......... A61K 9/0095 |
| | | | | 424/680 |

FOREIGN PATENT DOCUMENTS

| | | |
|---|---|---|
| DE | 3807 712 | 2/1986 |
| DE | 43 41 165 | 4/1995 |
| DE | 10 2006 001 199 | 7/2007 |
| EP | 0 192 367 | 8/1986 |
| GB | 1129260 | 10/1968 |
| HU | T54055 | 1/1991 |
| WO | 2004/078182 | 9/2004 |
| WO | 2005/099821 | 10/2005 |
| WO | 2006/094737 | 9/2006 |
| WO | 2006/134492 | 12/2006 |
| WO | 2007/057924 | 5/2007 |
| WO | 2009/036906 | 3/2009 |

* cited by examiner

*Primary Examiner* — Matthew P Coughlin
*Assistant Examiner* — Thurman Wheeler
(74) *Attorney, Agent, or Firm* — W&C IP

(57) ABSTRACT

The invention relates to polysiloxanes contained as defoaming agents, amongst other things, in medicinal compositions such colon cleansing solutions and antiflatulants. The aim of the invention is to further improve the defoaming effect of polysiloxanes and also the compatibility of the agents. According to the invention, the use of calcium sulphate increases the defoaming effect of dimeticon or simeticon as polysiloxane defoaming agents. The invention also relates to PEG-containing colon cleaning solutions based thereon.

9 Claims, No Drawings

COMPOSITIONS AND SOLUTIONS FOR COLON CLEANSING

The invention concerns compositions and solutions containing at least one polysiloxane, to be applied orally or rectally to humans and animals and to be used for bowel cleansing or as a prophylaxis or as a therapy for various types of dyspepsia, and finally, packaging units consisting of several concoctions resulting in the aforementioned compositions.

Polysiloxanes are important defoaming agents employed, among others, in medicine, food technology, and other applications. Among other things, they serve as technical lubricants, defoaming agents in paint and varnish, as antifoaming agents in preserves, canned food and deep-frying fat and in medicine as a drug to fight flatulence or as a laxative.

A frequently used representative of this group is polydimethylsiloxane (PDMS), a silicone of the general formula $R_3Si$—O—$(R_2Si$—O—$)$ n$SiR3$, with R=methyl. Die INN designation for PDMS is Dimeticon. Dimeticon is colorless, is considered non-toxic and chemically largely inert. It has been licensed as a food additive and a drug and, thanks to its defoaming properties, it is employed as a remedy for gas buildups in the gastrointestinal tract occurring in various types of dyspepsia (flatulence, meteorism). Polysiloxane is administered before imaging examinations of the gastrointestinal tract are employed to prevent shadowing effects by gas accumulations.

The defoaming property of Dimeticon is probably based on the fact that the presence of polar as well as nonpolar molecular zones cause an improved drainage of the foam lamellae and thus the disintegration of the foam.

Instead of Dimeticon Simeticon is used as well; same is a mixture of Dimeticon and highly disperse silicon dioxide. Generally, it contains 4-7 weight percent of $SiO_2$ in PDMS with a degree of polymerization between 200 and 400.

The use of Dimeticon against constipation, in particular among children, is known from DE 43 41 165 C1. There, a relatively high polysiloxane dosage was chosen. The effect could be based on the dissolving of flatulence, thus preventing or removing constipations caused by flatulent cramps. Dimeticon as well as Simeticon have been described as drugs against flatulence and bloating in WO 2005/099821 A1, among others.

From WO 2009/036906 A1 it has become knowledge to combine laxatives with defoaming agents, in particular with Dimeticon or Simeticon, in order to prevent flatulence as a side-effect of the laxatives and to better treat constipations. WO 2004/078182 A1 describes the use of Dimeticon or Simeticon as an anti-flatulence drug in combination with a dissolvable saccharide as a laxative.

DE 38 07 712 A1 manifests a dry preparation drug for the preparation of a laxative-acting beverage. It consists of a granulate with a fixed combination of PEG with a median molecular weight of at least 4000 Daltons, an alkaline hydrogen carbonate, citric acid and an electrolyte solution of sodium and potassium salts balanced against the body as a whole. The preparation may contain 0.1 to 0.2% of Dimeticon to suppress a possible foam generation during the preparation of the beverage and in the gastrointestinal tract, as well as commonly accepted additives such as artificial sweeteners, flavors and colorants. The laxative-acting drinking solution is suitable as a purely anti-constipation drug as well as a bowel-cleansing agent, i. e., an intestinal flushing solution before therapeutic or diagnostic procedures.

US 2005/0244368 A1 suggests the use of an electrolyte-free PEG composition for bowel cleansing, in particular for children. It elaborates that the known electrolyte-enriched PEG compositions proved to be unsafe, e.g. showing too many side effects, especially for the preparation of a colonoscopy.

Intestinal flushing solutions containing polyethylenglycol—INN designation Macrogol—have been in use in the USA and in Europe since at least 1984 and are increasingly replacing orthograde intestinal flushing solutions with simple-balanced electrolyte solutions on the basis of Mannitol. Intestinal flushing solutions are used for bowel cleansing in preparation of procedures at or examinations of the gastrointestinal tract. The purely saline intestinal flushing solutions were quite distressing for the patients, since large quantities of liquid had to be ingested, the salty solutions made their ingestion quite difficult and because their tolerability was limited.

The intestinal flushing solutions containing polyethylenglycol offered a considerable enhancement, ensured a faster and better bowel cleansing with less amounts of liquids and are generally tolerated much better. The addition of laxatives can largely dispensed with. In part, electrolytes, such as sodium sulfate, sodium bicarbonate, sodium chloride and potassium chloride are employed. Normally, the patient ingests between 2 and 6 liters of such an intestinal flushing solution. For an improved evacuation of gases from the gastrointestinal tract, Dimeticon or Simeticon can be added to these polyethylenglycol-enriched intestinal flushing solutions. This also and especially applies, if the intestinal flushing solution is not employed for the complete evacuation and cleansing of the bowels, but, to a small extent, is employed as an osmotic laxative.

Here, it is exploited that polyethylenglycol abundantly absorbs water, counteracting a solidification of the stool while same is passing through the bowels, and greatly facilitating the defecation.

The invention is based on the task of further improving the defoaming effect of polysiloxanes, especially within bowel cleansing and anti-constipation drugs, thus rendering these drugs more effective and tolerable.

Quite surprisingly it was found that the addition of calcium sulfate to compositions containing polysiloxane as defoaming agent resulted in a significant and unexpected improvement of the defoaming effect.

Therefore, in a first aspect, this invention provides the general use of calcium sulfate to enhance the defoaming effect of polysiloxanes.

The calcium sulfate employed for this purpose is preferably dihydrate, i. e. $CaSO_4.2H_2O$ (plaster). Alternatively, a use of hemihydrate $CaSO_4.1/2H_2O$ is possible as well. The subsequently indicated quantities always refer to the dihydrate. When using other calcium sulfate modifications or the hemihydrate, the respective calcium sulfate content has to be calculated.

The calcium sulfate is employed as a fine crystalline powder freely obtainable on the market. Further, the task includes a composition for oral or rectal application by humans and beasts, containing at least one polysiloxane with the added content of calcium sulfate of at least the similar weight of the polysiloxane or the sum of polysiloxanes. Here, the polysiloxane is employed as defoaming agent with the calcium sulfate acting as co-agent synergically supporting the effect of the polysiloxane defoaming agent.

Preferably, the polysiloxane defoaming agent(s) and calcium sulfate are used in a composition of 1:1 to 1:100 in weight. As a consequence, the calcium sulfate is present in the same amount or in excess of same.

Preferably, one dose of the composition (pill, capsule, powder and the like) contains 10 to 500 mg of polysiloxane and 500 to 1,000 mg of $CaSO_4$.

It is even more preferable for the polysiloxane to be Dimeticon or Simeticon.

Pursuant to an initial preferred type of embodiment, the composition may be in a solid form. The liquid polysiloxane, e.g., Dimeticon, is adsorbed by a solid calcium sulfate or compressed with a solid calcium sulfate combined with further, solid excipients (e.g., cellulose, lactose, glucose, etc.). For the application in solid form, a composition as a powder or granulate would be particularly appealing; this would permit a pre-portioning in individual doses by using sachets. Powder blends are preferably prepared for dissolving in water. Also quite suitable are effervescent tablets or effervescent powders, permitting a quick dissolving into a drinkable solution. By principle, the solid matter can be administered in any suitable galenic form, for instance as pills, granulate, sugar-coated tablets or capsules. In order to transport the polysiloxane and the calcium sulfate into the intestine, entericcoated pills, sugar-coated tablets and capsules are particularly suited.

In another preferred embodiment, the composition is part of a sustained release formulation, which ensures a little by little release of calcium sulfate and polysiloxane while passing through the intestine. Furthermore, the solid composition can also be incorporated in suppositories.

In capsules, the composition can be partially in solid and partially in a liquid form. For example, as already known as state of the art, the polysiloxane can be dissolved or distributed in a glycol, while the calcium sulfate is dispersed in it in solid form. The composition is thus a solid-liquid mixture within the dosage form. To give an example a rather more liquid solid-liquid mixture could be administered in a conventional liquid capsule like gelatin, for instance. For suppositories, the composition could be incorporated in conventional substrates, such as lipids.

As per a further aspect of the invention, the composition is present as a liquid, i.e., a liquid mixture, colloidal solution or suspension and is preferable offered as part of a capsule, a dripping solution, a syrup, juice or the like.

The composition may contain water, although the polysiloxanes are virtually insoluble in water and $CaSO_4$ dissolves in water in a very low extent only. To improve the homogeneity of the composition glycol and/or glycerin may be contained in it. Polysiloxane on the one hand and calcium sulfate on the other hand are contained in the compositions in a fixed-dose combination.

It is a well-known fact that calcium ions alone can have a defoaming effect. In such a case, however, they have to be part of highly aqueous (diluted) systems initially not found in the gastrointestinal tract. Calcium ions are also capable of precipitating lipids, which could otherwise serve as foam stabilizers. This is common knowledge from the lipid and tenside chemistries.

According to the current state of knowledge, a fundamental part of this invention is the fact that the calcium sulfate is transported into the intestine in its solid form or that it is present inside a liquid composition, i.e., a solution, in colloidal form, finely dispersed, at the border of liquefaction or in a supersaturated solution. This will be further detailed below in connection with solutions after the invention.

As a further part of the invention the composition contains at least on additional active agent, in particular at least one laxative. Suitable laxatives can be selected by a specialist from the usual laxatives. These are, among others:
 filler materials and bulking agents, such as plant fibers, inulin, various seeds;
 lubes, such as glycerin, paraffin;
 motility-enhancing materials, such as rhubarb, castor, sennoisides (*Senna* leaves)
 osmotically acting materials absorbing water and thus countermanding a stool dehydration, such as Epsom salts, Glauber salts, sugar alcohols (Sorbitol, Mannitol, Xylitol) and polyethylenglycol (INN name Macrogol).

To resolve the task, the invention also includes a packaging unit with several preparations containing the ingredients of the composition in line with one of the preparation examples and, administered in combination, offer all ingredients of the disclosed compositions.

The composition as per the invention described can, as presented, directly be administered orally or rectally; as a consequence, the polysiloxane can unfold its effect in combination with the calcium sulfate directly inside the body, and this inside the gastrointestinal tract including the rectum.

In another preferred embodiment it is envisaged that a composition in line with the invention for the production of a solution to be administered to humans or animals orally or rectally is used, which serves to cleanse the bowel or as a prophylaxis against or therapy of constipation, general digestive disorders such as dyspepsia or maldigestion, flatulence, meteorism, inflammatory and ulcerous conditions of the gastrointestinal tract, stomach cramps, borborygmus and the like. A solution to be administered orally, which was obtained from the composition is a drinking solution, a solution to be administered rectally is used for an enema. For this embodiment, the composition can be provided as a dry mixture or solid/liquid mixture and, mixed with water, prepared as a solution.

Apart from real solutions of the ingredients in the solvent, the term "solution" also covers supersaturated solutions, solutions with sediments, suspensions and especially colloidal solutions with finely dispersed calcium sulfate, if applicable with further not really dissolved but only suspended or emulsified ingredients.

In essence, the composition for the production of the solution can be present in a dry form or may be a solid/liquid mixture being a concentrate that is diluted with water to become the actual solution. Preferably, the resulting solution is an intestinal flushing solution as used in preparation for surgical procedures in the gastrointestinal tract or endoscopic examinations as well as ultrasound examinations. The solution may also be intended as an osmotic anti-constipation drug, i.e., for the facilitation of defecation without a complete bowel cleansing.

The invented solutions for oral or rectal administration to humans or animals for the purpose of bowel cleansing or the prophylaxis against or therapy of general digestive disorders, constipation, flatulence, meteorism, etc. contain polyethylenglycol, at least one polysiloxane and calcium sulfate in an aqueous solution, with the term "aqueous solution" covering pseudo-solutions, i.e., colloidal solutions containing solids or liquids in the colloidal form, suspensions and emulsions. Polysiloxanes basically insoluble in water for instance, as well as lubricants insoluble in water and the like are colloidally dissolved or emulsified as liquids. The solid calcium sulfate, which is also only slightly soluble in water (dissolubility approx. 2 g per liter at 20° C.), can be dissolved colloidally or suspended as well. The calcium sulfate is preferably used at its solubility limit. Therefore, during the preparation of the invented solution in particular when this occurs at higher temperatures it may be temporarily present in a dissolved state or in a supersaturated solution. If an additional sediment of calcium sulfate is present, the maximum ion concentration is present in the invented solution at the same time. Here, the calcium sulfate solubility product specifies the upper limit.

The invented solution offers a great variety of applications. Primarily, it constitutes an intestinal flushing solution. The intestinal flushing solution can be administered to patients requiring an orthograde bowel lavage before a colonoscopy, to patients requiring an intestinal flushing prior to an operation, i.e., a surgical procedure, to patients with an infectious colonization of the intestine with pathogens to be sanified by rinsing (e.g., *Salmonella enteritidis*), for the preparation of patients for radiology, e.g., before a double contrast barium imaging, for specialized Doppler examinations, for the preparation of emergency diagnostics, in particular in case of rectal hemorrhages and in acute toxic conditions as gastrointestinal decontamination techniques.

The intestinal flushing solution is unchanged in its composition but, if necessary with a reduced overall liquid quantity, can also be employed for the treatment of constipations, namely chronic or acute constipations up to very serious constipations, such as coprostasis. With certain diseases a facilitated defecation is required as well, causing the invented solutions to be indicated, for instance in case of postoperative constipations and constipations caused by medication (e.g., opiate constipations). A further indication for the invented intestinal flushing solution are the prophylaxis against and therapy of the portocaval encephalopathy. For quite some time now, polyethylenglycol-containing intestinal flushing solutions have proven to be particular advantageous, also for the purposes mentioned above among others. One of the advantages of using such compositions lies in the reduction of the preparation time from usually three days in the past to one to two days with a minimum of 4-5 hours. The patient is required to ingest between two and six liters of the prepared intestinal flushing solution. This flushing quantity of several liters serves to completely empty and cleanse the intestine, with the possible side effect that the solution might deprive the body of important substances. This must be avoided. In order to avoid the absorption of water and electrolytes from the intestinal wall by the intestinal lumen, intestinal flushing solutions are frequently enriched with electrolytes. Increased losses of electrolytes represent considerable risks. With high electrolyte losses, the application of an intestinal flushing solution would no longer be safe and could, at worst, be life-threatening.

Therefore, a net zero migration of water and electrolytes is aimed at. For this purpose attempts are being made to establish iso-osmolarity between the prepared solution and the intra- or extracellular liquid of the intestinal wall, respectively.

A very advantageous intestinal flushing solution already containing—apart from polyethylenglycol—Dimeticon or Simeticon as a polysiloxane defoaming agent, is already known from DE 10 2006 001 199 A1.

It is expressly referred to the technical contents of this document. Within the scope of this present invention, the intestinal flushing solutions known from DE 10 2006 001 199 A1 are complemented with calcium sulfate as an agent to increase the defoaming effect. The disclosure of DE 10 2006 001 199 A1 is therefore included by reference into the present disclosure.

It is an important aspect of the invention that the solution as described above is virtually saturated with respect to the calcium sulfate, with the solubility product of calcium sulfate not falling short by more than 10%, or that the solution with respect to calcium sulfate is supersaturated or that it is present as a suspension or colloidal solution with finely dispersed calcium sulfate. A sedimentation of calcium sulfate is possible; before administering, the sediment can be reslurried by agitation and thus administered as well.

In all solutions of the invention, i.e., intestinal flushing solutions or solutions as anti-constipation drugs, the polyethylenglycol should have a molecular weight between 2,000 Da and 6,000 Da, preferably between 3,000 Da and 4,000 Da and even more preferably between 3,350 Da and 4,000 Da. Macrogol with these molecular weights have been tried and tested for respective purposes. As per one aspect of the invention, the solutions may contain at least one electrolyte in addition, selected from the group of physiologically compatible potassium, sodium and magnesium salts, with the exception of such anions that—together with calcium—can create sparingly soluble salts in water, and in particular with the exception of sulfates, carbonates and oxalates. Electrolytes provided for the generation of iso-osmolarity inside the intestine, are therefore preferably employed as chlorides and/or hydrogen carbonates. Since only very little amounts of calcium sulfate dissolve in water, the electrolyte effect is only marginally changed by the calcium sulfate; in any case, the change can be easily taken into consideration. The use of Epsom salts and Glauber salts is consequently avoided, which is indicated already due to the unpleasant bitter taste. It turned out that preparations containing sulfates show a low tolerability and frequently cause vomiting.

Instead of Epsom salt and Glauber salt, however, other laxatives may be added. Preferably, these are lubricants, neutral swelling agents or anti-flatulence products such as in particular those on a vegetable base. Examples would be caraway oil, fennel oil, peppermint oil, anise oil, chamomile extract, and myrrh. The invented intestinal flushing solutions may contain further substances, which, however, should not take any influence on the electrolyte balance and should not have a cramp-triggering or flatulent effect. Further possible substances contained could be in particular detoxification products, antiemetics or propulsives.

In an alternative aspect of the invention, intestinal flushing solutions are provided that have not been complemented with electrolytes. These compositions as well have their applications as described in US 2005/0244368 A 1, for instance.

In addition, the solutions of this invention may contain additives and excipients, such as flavors, artificial sweeteners, coloring agents, stabilizers, preservatives, vitamins and the like.

In the following, the invention will be explained in detail based on examples, which solely serve the purpose of better illustrating the invention. Based on the description above the expert can easily find additional examples. The invention is not limited to the listed examples.

EXAMPLES

Description of the Ingredients

Polyethylenglycols (Macrogol) are commercially available. Those with molecular weights of 2,000 Da to 6,000 Da are suitable in the context of this invention. Polyethylenglycols with molecular weights between 3,000 Da and 4,000 Da seem to be particularly suitable. In the examples, a polyethylenglycol with a molecular weight of 3,350 Da (PEG 3350) was uses. Polyethylenglycols are solid substances; they are used in a powdery form.

The electrolytes are simple salts and are employed as fine crystalline solids in a mostly pure form. They are all commercially available. In the examples an electrolyte blend of sodium and potassium salts is being used; individually, sodium chloride, potassium chloride and sodium hydrogen carbonate are being employed.

Polysiloxanes: Dimeticon as well as Simeticon were examined. The INN designation stands for a-(trimethylsilyl)-ω-methylpoly(oxydi-methylsilylen)), INCI: dimethicones. Liquid, virtually insoluble in water, mixes with glycol and glycerol.

Simeticon is a blend of Dimeticon and silicon dioxide. The silicon dioxide is present in finely dispersed, preferably nanodispersed form (pyrogenic silicic acid). The silicon dioxide content may vary. INCI: Simethicone. A suspension of silicon dioxide in Dimeticon, viscous liquid and gray-white opalescent.

In the examples, the calcium sulfate is employed as dihydrate in finely crystalline form. It is commercially available. Calcium sulfate is permitted as a food additive and may be used here in this quality or as a pharmaceutical raw material in a respective quality.

The solubility product of calcium sulfate is $2.3 \times 10^{-4}$ (mol$^2$/L$^2$). This solubility product $K_L=[Ca^{2+}][SO_4^{2+}]$ would be influenced by additional calcium and sulfate ions present in the solutions from other sources. Therefore, the solutions in the examples are being prepared with demineralized water.

Example #1

To be dissolved in 500 ml demineralized water

| | |
|---|---|
| 52.5 g | polyethylenglycol 3350 |
| 0.715 g | sodium hydrogen carbonate |
| 1.400 g | sodium chloride |
| 0.185 g | potassium chloride |

Into these solutions and under fast agitation 0.25 g of Simeticon was dripped into 0.5 g of glycerol. In addition, 1 g of finely crystalline calcium sulfate dihydrate was stirred in.

The solutions is to be used fresh, i.e., within 20 minutes from preparation.

Example #2

Example 1 was complemented with 0.5 g of saccharine sodium as sweetener and 0.5 g of a fruit flavor.

Example #3

1 g of finely crystalline, dry calcium sulfate is impregnated with 0.35 g of Simeticon. The mixing process can be effected in a vibratory mill. The calcium sulfate impregnated with Simeticon is strongly stirred into 500 ml of demineralized water, which has been spiked before with 60 g of PEG 3350.

The mixture is continuously agitated for 10 more minutes and used within 20 minutes.

Example #4

1 g of finely crystalline dry calcium sulfate is impregnated with 0.25 g of Dimeticon. The mixing process can be effected in a vibratory mill. The calcium sulfate impregnated with Dimeticon is strongly stirred into 500 ml of demineralized water, which has been spiked before with 60 g of PEG 3350.

The mixture is continuously agitated for 5 more minutes and used within 20 minutes.

Tests

In vitro testing in various flushing solutions was made regarding the foam generation. As a basis, commercially available Macrogol flushing solutions were employed. During a standardized shaking test (Bartsch test) the unmodified solutions were compared with solutions that 1) additionally contained Simeticon, 2) additionally contained CaSO$_4$, but no Simeticon, 3) additionally contained CaSO$_4$ as well as Simeticon. The results are described in the following:

The foam generation was determined by the short-term Bartsch test. For this purpose 5 ml of the test solution were filled into a calibrated test tube with a diameter of 15 mm and a capacity of 20 ml. Immediately following that the test tube is shaken in a standardized fashion 10 times for 7 s each and the volume of the foam generated by this shaking is measured. In addition, the time is measured until the solution becomes visible for the first time or the stable remaining volume is determined after 5 minutes. The following lavage solutions were examined in vitro (parent solutions):

A: Endofalk Classic, active substances: potassium chloride, sodium chloride, sodium hydrogen carbonate, Macrogol 3350, B: Medicoforum Cleansing, active substances: potassium chloride, sodium chloride, sodium hydrogen chloride, Macrogol 3350, quantitative composition as described in example #1, C: Klean-Prep, active substances: potassium chloride, sodium chloride, sodium sulfate, sodium hydrogen carbonate, Macrogol 3350, aspartame, vanilla flavor, D: Moviprep Orange, active substances: potassium chloride, sodium chloride, sodium sulfate, ascorbic acid, sodium ascorbate, Macrogol 3350.

The parent solutions A to D were composed in accordance with the instructions in the package leaflet at room temperature (22° C.) and in the prescribed concentrations. 500 ml of parent solutions each were prepared.

Of these parent solutions A-D, 5 ml each were used for the Bartsch test.

If the residual foam after 5 min is still sufficiently stable, 0.2 ml of Simeticon (equivalent to approx. 5 mg of Simeticon) are added to 500 ml of the test solution in a second series and the short-term Bartsch test is repeated. Each test is conducted 10 times and the mean values and standard deviations are calculated. Statistical analyses were conducted with a Student-t test. Significant differences were found at a $p<0.05$.

TABLE #1

Foam volume and dissolution times with and without Simeticon in the standard solutions (n = 10)

| | Foam volume (ml) | dissolution time (sec) |
|---|---|---|
| | Mean values and standard deviations | |
| Solution A | | |
| w/o Simeticon | 1.30 +/− 0.13 | 88 +/− 11.6 |
| with Simeticon | 0.20 +/− 0.60 | 4 +/− 3.0 |
| Solution B | | |
| w/o Simeticon | 1.20 +/− 0.90 | 187 +/− 79 |

TABLE #1-continued

Foam volume and dissolution times with and without Simeticon in the standard solutions (n = 10)

|  | Foam volume (ml) | dissolution time (sec) |
|---|---|---|
|  | Mean values and standard deviations | |
| with Simeticon Solution C | 0.10 +/− 0.15 | 11 +/− 1.50 |
| w/o Simeticon Solution D | 2.30 +/− 0.40 | 147 +/− 30.0 |
| with Simeticon | 0.10 +/− 0.10 | 7 +/− 0.90 |
| w/o Simeticon | 1.20 +/− 0.20 | 70 +/− 60 |
| with Simeticon | 0.10 +/− 0.03 | 6 +/− 2.00 |

Results from the Comparison of Parent Solutions with and without Simeticon

After the Bartsch test, all solutions A to D displayed a fine bubbly foam ball generation of approx. 30% of the test solutions' volume, which remained stable for about 120 s. Most of the foam was generated in solution C with 2.34 ml and a time span of 147 s until the solution became visible (table 1). More stable, however, was the foam of solution 8 with a dissolution time of 187 s. The pure Macrogol solutions A-D all presented a high propensity to generate foam. By adding 0.2 ml (5 mg) of Simeticon, in all solutions A-D a foam generation was largely prevented. The foam contained coarse bubbles and dissolved quickly. On average, the foam volumes were 0.13 ml and the foam dissolution time 7 s (table 1). All differences were highly significant ($p<0.0001$).

Effects of Calcium Sulfate on the Parent Solutions with and without Simeticon.

General Influences on the Flushing Solution 1 g of calcium sulfate in 500 ml of flushing solution changes the taste; same becomes more calcareous and blunt. Calcium sulfate must be stirred in well and parts of it will precipitate again, if left untouched for approx. 30 min.

Below the test results for parent solution B are described, the foam of which was the most stable in the comparative tests.

TABLE #2

|  | Foam volume (ml) n = 10 | dissolution time (sec) (n = 10) |
|---|---|---|
| (1) Parent solution B without additives | 1.27 +/− 0.27 | 125 +/− 48 |
| (2) Parent solution B with $CaSO_4$ | 0.84 +/− 0.13 | 52.4 +/− 30 |
| (3) Parent solution B with Simeticon and $CaSO_4$ | 0.00 | 0.00 |
| Significance | p < 0.0002 | p < 0.0001 |

1 g of $CaSO_4$ and 0.2 ml of Simeticon in 500 ml of parent solution test volume 5 ml.

Mean values from 10 tests, n=10.

Results:

Solution (2) already—only parent solution with $CaSO_4$ generates significantly less foam, which, in addition, is significantly less stable. This effect, however, is considerably less pronounced than that of Simeticon (refer to table #1). Completely convincing are the results from solution (3) only. Here, $CaSO_4$ as well as Simeticon were used for defoaming. No measurable foam was produced.

Discussion

The parent flushing solutions produce a fine bubbly ball-shaped foam of up to 30% of their own volume, which, over time, shows a relative stability.

For the tests, only small volumes of the solutions were used. An extrapolation to the volumes of 2,000 to 3,000 ml that would normally be used would result in a substantial foam volume of 600-1,000 ml in the preparatory course of approx. 16 hours. This could explain flatulence and abdominal complaints with cramps among some of the patients. The addition of Simeticon already prevents the generation of foam to a great extent.

The solution containing calcium sulfate and Simeticon did not produce any measurable foam. Compared to a respectively prepared solution without calcium sulfate, the taste of the solution was changed marginally only. Therefore, the new solutions should be well accepted by the patients. The relevant side effects caused by foam generation—such as bloatedness, flatulence and nausea are minimized.

The invention claimed is:

1. A method for the prophylaxis against or therapy of digestive disorders, flatulence, meteorism, stomach cramps or borborygmus caused by intestinal foam generation, comprising administering orally or rectally to a human or animal in need thereof an aqueous liquid solution comprising polyethyleneglycol, at least one polysiloxane and calcium sulfate, wherein said aqueous liquid solution is saturated with respect to the calcium sulfate, and wherein said aqueous liquid solution comprises 10 to 500 mg of the at least one polysiloxane and 500 to 1000 mg calcium sulfate.

2. The method according to claim 1, wherein the polyethyleneglycol has a molecular weight ranging from 2,000 Daltons to 6,000 Daltons.

3. The method according to claim 1, wherein said aqueous liquid solution contains at least one electrolyte, selected from the group of physiologically tolerable potassium, sodium and magnesium salts with the exception of such anions capable of forming poorly soluble salts with calcium in water and with the exception of sulfates, carbonates, and oxalates.

4. The method according to claim 1, wherein said aqueous liquid solution further comprises at least one additional active substance selected from the group consisting of laxatives, lubricants, anti-flatulent drugs, detoxification preparations, antiemetics, and propulsives.

5. The method according to claim 1, wherein said aqueous liquid solution further comprises additives and excipients selected from the group consisting of flavors, artificial sweeteners, colorants, stabilizers, preservatives and/or vitamins.

6. The method according to claim 1, wherein said at least one polysiloxane is Dimeticon or Simeticon.

7. The method according to claim 2, wherein the polyethyleneglycol has a molecular weight ranging from 3,000 Daltons to 4,000 Daltons.

8. The method according to claim 3, wherein said potassium, sodium and magnesium salts are chlorides or hydrogen carbonates.

9. A method for the prophylactic treatment of a patient suffering from digestive disorders, flatulence, meterorism, stomach cramps or borborygmus caused by intestinal foam generation in a human or animal subject, comprising orally or rectally administering to the human or animal subject an aqueous solution comprising polyethyleneglycol, calcium sulfate, and at least one polysiloxane, wherein said aqueous solution is saturated with respect to calcium sulfate, wherein said aqueous solution comprises 10 to 500 mg of the at least one polysiloxane and 500 to 1000 mg calcium sulfate, and wherein the aqueous solution is administered in a dose sufficient to eliminate or reduce intestinal foam generation in said human or animal subject.

* * * * *